United States Patent

Inukai et al.

[11] 4,279,770
[45] Jul. 21, 1981

[54] LIQUID CRYSTAL 2,3-DICYANO-HYDROQUINONE DERIVATIVES

[75] Inventors: Takashi Inukai; Hiromichi Inoue; Kenji Furukawa; Hideo Sato; Shigeru Sugimori, all of Yokohamashi, Japan

[73] Assignee: Chisso Corporation, Osaka, Japan

[21] Appl. No.: 74,655

[22] Filed: Sep. 12, 1979

[30] Foreign Application Priority Data

Sep. 20, 1978 [JP] Japan .................. 53-115591
Nov. 15, 1978 [JP] Japan .................. 53-140710
Nov. 25, 1978 [JP] Japan .................. 53-145508
Jan. 31, 1979 [JP] Japan .................. 54-9917
Mar. 24, 1979 [JP] Japan .................. 54-34545
Aug. 27, 1979 [JP] Japan .................. 54-108978

[51] Int. Cl.³ .................. C07C 121/75; C09K 3/34; G02F 1/13
[52] U.S. Cl. .................. 252/299.62; 260/465 D; 350/350 R; 252/299.63; 252/299.64; 252/299.65
[58] Field of Search .................. 260/465 D; 252/299

[56] References Cited

U.S. PATENT DOCUMENTS 3,915,883 10/1975 Van Meter et al. .................. 252/299
4,099,856 7/1978 Weissflog et al. .................. 350/350

FOREIGN PATENT DOCUMENTS 562547 6/1977 U.S.S.R.

OTHER PUBLICATIONS

Baptista et al., J.C.S. Perkin I, pp. 1477-1500, (1977).
Zielinski et al., Chemical Abstracts, vol. 90, 112982m, (1979).

Primary Examiner—Dolph H. Torrence
Attorney, Agent, or Firm—Fred Philpitt

[57] ABSTRACT

Liquid crystal materials for liquid crystal display, having a large negative dielectric anisotropy and maintaining a liquid crystal state at a broad temperature range including room temperature are provided. These materials contain novel compounds expressed by the general formula (I)

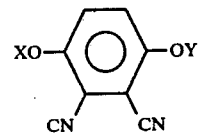

wherein
X represents

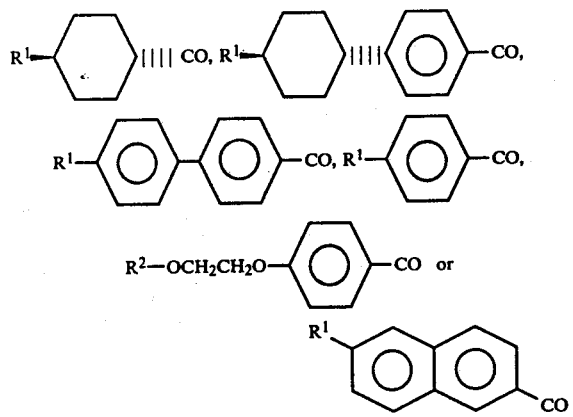

Y represents

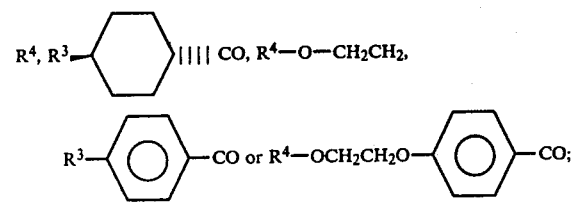

$R^1$ and $R^3$ each represent an alkyl group or an alkyloxy group of 1-10 carbon atoms;

$R^2$ and $R^4$ each represent an alkyl group of 1–10 carbon atoms; but compounds wherein $X = R^1$--CO and $Y = R^4$ or $R^3$-⬡-CO are excluded.

10 Claims, 3 Drawing Figures

FIG. 2

FIG. 3

LIQUID CRYSTAL 2,3-DICYANO-HYDROQUINONE DERIVATIVES

DESCRIPTION OF THE INVENTION

The present invention relates to novel liquid crystal materials for liquid crystal display. More particularly it relates to liquid crystal materials having a large negative value of dielectric anisotropy.

Among the compounds included in the present invention, some compounds themselves exhibit an enantiotropic mesophase, a part thereof themselves exhibit a monotropic mesophase and others themselves exhibit no mesophase. Any one of these compounds, however, can be employed for preparing liquid crystal materials having a large negative value of dielectric anisotropy, by mixing the compounds with other liquid crystal materials. The present invention includes a group of compounds having a liquid crystal property or a non-liquid-crystal property, to be employed for preparing liquid crystal materials having a large negative value of dielectric anisotropy and liquid crystal compositions having a large negative value of dielectric anisotropy.

It has been generally known that nematic liquid crystal materials having a negative value of dielectric anisotropy are important constituting elements for liquid crystal display cells of light-scattering type wherein formation of a dynamic scattering in a liquid crystal layer is effected by impressing a voltage; liquid crystal display elements of so-called DAP type wherein a multicolor display is carried out by means of a polarizing plate utilizing the birefringence of liquid crystal by controlling the inclination of liquid crystal molecules; color display elements of so-called guest-host type wherein a liquid crystal material having a specified dye contained is employed; etc.

In the above-mentioned liquid crystal display apparatuses, for reducing the lowest voltage necessary for initiating the response of a liquid crystal to the impression of a voltage, i.e. a threshold voltage, and for reducing the voltage necessary for exhibiting a sufficient contrast of the display to vision, i.e. an actuating voltage, it is required that the dielectric anisotropy ($\Delta\epsilon$) of liquid crystal materials have a large negative value. However, for example, MBBA (methoxybenzylidenebutylaniline) which is well known as a liquid crystal having a negative dielectric anisotropy, has a $\Delta\epsilon$ of about $-0.5$, and a liquid crystal consisting of phenyl esters of benzoic acid which is also well known as such has a $\Delta\epsilon$ of about $-0.4$ at the highest. Accordingly, advent of a liquid crystal substance having a $\Delta\epsilon$ of a larger negative value has been desired.

As one of the substances satisfying such a desire, a substance having a cyano group on the side of a molecule has been proposed.

Namely, bis-(4'-n-alkylbenzylidene)-2-cyano-1,4-phenylenediamines (II)

(Japanese patent application laid-open No. 71393/1977) and 4-alkyl-2-cyanophenyl esters of 4-alkyl-4'-biphenylcarboxylic acid (III)

(Japanese patent application laid-open No. 118450/1977) are known.

Further, substances having two cyano groups on the side of a molecule as shown in the following formula (IV) have recently been proposed:

(IV)

(wherein a substance of $n=4$ has a C-N point of 164° C. and a N-I point of 195° C. and that of $n=6$ has a C-N point of 146° C. and a N-I point of 168° C.) (U.S.S.R. Pat. No. 562547).

It is true that either of the substances of the formulas (II) and (III) have a $\Delta\epsilon$ of a large negative value (about $-4 \sim -5$) than those of the above-mentioned MBBA, etc., but their mesomorphic temperature ranges are considerably higher than room temperature; hence it is impossible to employ them alone, and for maintaining a liquid crystal state at room temperature, they are employed in admixture with other liquid crystal materials having their mesomorphic temperature range at room temperature. However, when these materials are added in an amount to such an extent that the reduction in the actuating voltage as mentioned above is brought about, undesirable effects upon other physical properties such as response rate appear. This is presumed to be brought about by the fact that since these substances (II) and (III) have a relatively high molecular weight, their viscosities increase. Accordingly, for reducing the amount of a substance having a negative $\Delta\epsilon$ value added and yet obtaining a sufficient effectiveness, advent of a substance having a larger negative $\Delta\epsilon$ value has been desired. Further, since the compound (IV) has a $\Delta\epsilon$ of about $-7$ and a high C-N point, its amount to be admixed into a liquid crystal mixture at room temperature is severely restricted.

In the case of the guest-host type display, liquid crystals having a negative $\Delta\epsilon$ preferable to those having a positive $\Delta\epsilon$. The reason is as follows:

In the case of liquid crystals having a positive $\Delta\epsilon$, they are arranged in a parallel (or homogeneous) alignment in advance, and then turned into a vertical (or homeotropic) alignment by applying a voltage. On the other hand, dichroic dyes generally have a positive dichroism. What is meant by positive dichroism is that the direction of the transition moment of absorption of a visible light accords completely or almost completely with the direction of the principal axis of a dye molecule. Accordingly, a portion having no voltage impressed is colored, whereas a portion having a voltage impressed becomes colorless. Thus, in the guest-host display in this manner, colorless picture elements such as letters, numeral figures, etc. are displayed on a colored background; so to speak, a negative display is brought about. On the other hand, in the case of liquid crystals having a negative $\Delta\epsilon$, since they are, in advance, brought into a vertical alignment, if a usually easily available dye having a positive dichroism is em- ployed, they are colorless in the state where no voltage is impressed, and only when a voltage is impressed, they are colored; hence picture elements such as letters, numeral figures, etc. are color-displayed on the colorless background. Namely, a positive color display which is attractive is brought about. Of course, if a dye having a negative dichroism is employed as a guest dye, an utterly contrary display to the above-mentioned is brought about. However, such dyes having a negative dichroism are difficult to obtain, and their color tones are restricted only to a narrow range. Accordingly, for the liquid crystal display for guest-host type display, liquid crystals having a negative Δε are preferable. Further, in order to actuate them in a semiconductor circuit, a liquid crystal material having a larger negative Δε value is required.

In view of the foregoing situation, the present inventors have made studies with the object of obtaining a liquid crystal material having a larger negative value of dielectric anisotropy and yet maintaining a liquid crystal state in a broad temperature range including room temperature, and in these studies, have searched for a substance which is more suitable as a constituting component of such liquid crystal materials than the above-mentioned compounds of the formulas (II), (III) and (IV). As a result, the present inventors have found that a group of compounds among those having two CN groups on the same side of a molecule as in the compounds of the formula (IV) become an extremely suitable constituting component, and have completed the present invention.

The present invention resides in:
Compounds expressed by the general formula (I)

(I)

wherein
X represents

Y represents $R^1$ and $R^3$ each represent an alkyl group or an alkyloxy group of 1-10 carbon atoms;
$R^2$ and $R^4$ each represent an alkyl group of 1-10 carbon atoms; but
compounds wherein are excluded.

Concrete examples of these compounds and the mesomorphic temperature ranges thereof are shown in Tables 1–11, and those of compounds which are similar and related to those of the present invention but outside the scope thereof are shown in Table 12.

TABLE 1

Compounds of the formula (I) wherein X = $R^1$-⟨⟩||||CO and Y = $R^4$

| Compound No. | $R^1$ | $R^4$ | C-N point or C-I point (°C.) | N-I point or S-I point (°C.) |
|---|---|---|---|---|
| 1 | $C_6H_{13}O$ | $C_2H_5$ | 116.2 | — |
| 2 | $C_3H_7$ | $C_3H_7$ | 95.0 | — |
| 3 | $C_4H_9$ | $C_3H_7$ | 88.5 | — |
| 4 | $C_5H_{11}$ | $C_3H_7$ | 89.5 | (46.0) |
| 5 | $C_6H_{13}$ | $C_3H_7$ | 90.5 | (50.0) |
| 6 | $C_7H_{15}$ | $C_3H_7$ | 95.0 | (40.0) |
| 7 | $C_6H_{13}O$ | $C_3H_7$ | 94.5 | — |
| 8 | $C_3H_7$ | $C_4H_9$ | 95.0 | (39) |
| 9 | $C_4H_9$ | $C_4H_9$ | 89.1 | (77.4) |
| 10 | $C_5H_{11}$ | $C_4H_9$ | 92.7 | (78.8) |
| 11 | $C_6H_{13}$ | $C_4H_9$ | 87 | (70) |
| 12 | $C_7H_{15}$ | $C_4H_9$ | 88 | (64) |
| 13 | $C_4H_9O$ | $C_4H_9$ | 80.3 | — |
| 14 | $C_6H_{13}O$ | $C_4H_9$ | 81.7 | — |
| 15 | $C_3H_7$ | $C_5H_{11}$ | 87 | (55) |
| 16 | $C_4H_9$ | $C_5H_{11}$ | 83 | (67) |
| 17 | $C_5H_{11}$ | $C_5H_{11}$ | 101.5 | (77) |
| 18 | $C_6H_{13}$ | $C_5H_{11}$ | 93 | (83) |
| 19 | $C_7H_{15}$ | $C_5H_{11}$ | 95 | (85) |
| 20 | $C_4H_9O$ | $C_5H_{11}$ | 62.5 | — |
| 21 | $C_5H_{11}O$ | $C_5H_{11}$ | 61.5 | — |
| 22 | $C_6H_{13}O$ | $C_5H_{11}$ | 80.4, 96.6 | (66.4) (S-I) |
| 23 | $C_3H_7$ | $C_6H_{13}$ | 80.4 | (59 ~ 62) (S-I) |
| 24 | $C_4H_9$ | $C_6H_{13}$ | 65 ~ 67 (C-S) | 76.7 ~ 77.2 (S-I) |
| 25 | $C_5H_{11}$ | $C_6H_{13}$ | 79 (C-S) | 88.5 (S-I) |
| 26 | $C_6H_{13}$ | $C_6H_{13}$ | 92 (C-S) | 92.8 (S-I) |
| 27 | $C_7H_{15}$ | $C_6H_{13}$ | 100.6 | (89 ~ 89.5) (S-I) |
| 28 | $C_3H_7$ | $C_7H_{15}$ | 85.5 | (72) (S-I) |
| 29 | $C_4H_9$ | $C_7H_{15}$ | 74.5 (C-S) | 84.2 (S-I) |
| 30 | $C_5H_{11}$ | $C_7H_{15}$ | 72.5 (C-S) | 94.0 (S-I) |
| 31 | $C_6H_{13}$ | $C_7H_{15}$ | 75.8 (C-S) | 98.3 (S-I) |

TABLE 2

Compounds of the formula (I) wherein X = $R^1-\bigcirc|||| CO$ and Y = $R^3-\bigcirc|||| CO$

| Compound No. | $R^1$ | $R^3$ | C-N point or C-I point (°C.) | N-I point (°C.) |
|---|---|---|---|---|
| 32* | H | H | 120.5 | — |
| 33 | $C_3H_7$ | $C_3H_7$ | 137 | 215 |
| 34 | $C_4H_9$ | $C_4H_9$ | 138 | 210 |
| 35 | $C_5H_{11}$ | $C_5H_{11}$ | 137 | 214 |
| 36 | $C_6H_{13}$ | $C_6H_{13}$ | 131.5 | 206 |
| 37 | $C_8H_{17}$ | $C_8H_{17}$ | 119 | 203 |
| 38 | $C_6H_{13}O$ | $C_6H_{13}O$ | 126 | 180 |

*The Compound of No. 32 is outside the scope of those of the present invention.

TABLE 3

Compound of the formula (I) wherein X = $R^1-\bigcirc|||| CO$ and Y = $R^4OCH_2CH_2$

| Compound No. | $R^1$ | $R^4$ | C-N point or C-I point (°C.) | N-I point (°C.) |
|---|---|---|---|---|
| 39 | $C_3H_7$ | $C_3H_7$ | 57.6 | — |
| 40 | $C_4H_9$ | $C_3H_7$ | 60.4 | — |
| 41 | $C_5H_{11}$ | $C_3H_7$ | 57.5 | — |
| 42 | $C_5H_{11}$ | $C_2H_5$ | 77.5 | — |
| 43 | $C_6H_{13}O$ | $C_3H_7$ | 71.5 | — |

TABLE 4

Compound of the formula (I) wherein X = $R^1-\bigcirc||||\bigcirc-CO$ and Y = $R^4$

| Compound No. | $R^1$ | $R^4$ | C-N point or C-I point (°C.) | N-I point (°C.) |
|---|---|---|---|---|
| 44 | $C_2H_5$ | $C_4H_9$ | 134.5 | — |
| 45 | $C_2H_5$ | $C_5H_{11}$ | 137.5 | — |
| 46 | $C_3H_7$ | $C_3H_7$ | 152 | (131.5) |
| 47 | $C_3H_7$ | $C_4H_9$ | 150 | (138) |
| 48 | $C_3H_7$ | $C_5H_{11}$ | 142 | (133) |
| 49 | $C_3H_7$ | $C_6H_{13}$ | 152.5 | (130) |
| 50 | $C_3H_7$ | $C_7H_{15}$ | 149 | (122.5) |
| 51 | $C_3H_7$ | $C_8H_{17}$ | 152 | (120.5) |
| 52 | $C_4H_9$ | $C_4H_9$ | 125 | 138 |
| 53 | $C_4H_9$ | $C_5H_{11}$ | 126 | 134.5 |
| 54 | $C_5H_{11}$ | $C_3H_7$ | 142 | 144.5 |
| 55 | $C_5H_{11}$ | $C_4H_9$ | 137.5 | 145.5 |
| 56 | $C_5H_{11}$ | $C_5H_{11}$ | 133 | 143.5 |
| 57 | $C_5H_{11}$ | $C_6H_{13}$ | 142.5 | (141) |
| 58 | $C_5H_{11}$ | $C_7H_{15}$ | 137 | (134) |
| 59 | $C_6H_{13}$ | $C_5H_{11}$ | 128 | 134 |
| 60 | $C_7H_{15}$ | $C_3H_7$ | 144.5 | (138.5) |
| 61 | $C_7H_{15}$ | $C_4H_9$ | 139 | 141.5 |
| 62 | $C_7H_{15}$ | $C_5H_{11}$ | 135 | 139.5 |
| 63 | $C_7H_{15}$ | $C_6H_{13}$ | 141.5 | (138.5) |
| 64 | $C_7H_{15}$ | $C_7H_{15}$ | 135.5 | (134.5) |

TABLE 5

Compounds of the formula (I) wherein X = $R^1-\bigcirc||||\bigcirc-CO$ and Y = $R^4-OCH_2CH_2$

| Compound No. | $R^1$ | $R^4$ | C-N point (°C.) | N-I point (°C.) |
|---|---|---|---|---|
| 65 | $C_3H_7$ | $C_3H_7$ | 105.5 | (63) |
| 66 | $C_5H_{11}$ | $C_2H_5$ | 85 | 98.6 |
| 67 | $C_5H_{11}$ | $C_3H_7$ | 97.5 | (84) |
| 68 | $C_7H_{15}$ | $C_3H_7$ | 101.2 | (88) |

TABLE 6

Compounds of the formula (I) wherein X = $R^1-\bigcirc-\bigcirc-CO$ and Y = $R^4$

| Compound No. | $R^1$ | $R^4$ | C-N point or C-I point (°C.) | N-I point (°C.) |
|---|---|---|---|---|
| 69 | $C_5H_{11}$ | $C_4H_9$ | 150.8 | 153.6 |
| 70 | $C_5H_{11}$ | $C_5H_{11}$ | 149.3 | 149.8 |
| 71 | $C_7H_{15}$ | $C_4H_9$ | 146.9 | 148.5 |
| 72 | $C_7H_{15}$ | $C_5H_{11}$ | 147 | 148 |

TABLE 7

Compounds of the formula (I) wherein X = $R^1-\bigcirc-\bigcirc-CO$ and Y = $R^4-OCH_2CH_2$

| Compound No. | $R^1$ | $R^4$ | C-N point or C-I point (°C.) | N-I point |
|---|---|---|---|---|
| 73 | $C_5H_{11}$ | $C_2H_5$ | 137.8 | — |
| 74 | $C_5H_{11}$ | $C_3H_7$ | 130.8 | — |

TABLE 8

Compounds of the formula (I) wherein X = $R^1-\bigcirc\bigcirc-CO$ and Y = $R^4$

| Compound No. | $R^1$ | $R^4$ | C-N point or C-I point (°C.) | N-I point |
|---|---|---|---|---|
| 75 | $C_5H_{11}$ | $C_4H_9$ | 140.2 | — |
| 76 | $C_5H_{11}$ | $C_5H_{11}$ | 135.8 | — |
| 77 | $C_5H_{11}O$ | $C_4H_9$ | 133.1 | — |
| 78 | $C_5H_{11}O$ | $C_5H_{11}$ | 122.6 | — |
| 79 | $C_7H_{15}$ | $C_4H_9$ | 132.3 | — |
| 80 | $C_7H_{15}$ | $C_5H_{11}$ | 135.0 | — |
| 81 | $C_8H_{17}O$ | $C_4H_9$ | 128.1 | — |
| 82 | $C_8H_{17}O$ | $C_5H_{11}$ | 122.7 | — |

TABLE 9

Compounds of the formula (I) wherein X = $R^2-OCH_2CH_2O-\bigcirc-CO$ and Y = $R^4-OCH_2CH_2O-\bigcirc-CO$

| Compound No. | $R^2$ | $R^4$ | C-N point or C-I point (°C.) | N-I point |
|---|---|---|---|---|
| 83 | $C_3H_7$ | $C_3H_7$ | 115.8 | — |
| 84 | $C_4H_9$ | $C_4H_9$ | 116 | — |

TABLE 9-continued

Compounds of the formula (I) wherein X =

R²—OCH₂CH₂O—⟨⟩—CO and Y = R⁴—OCH₂CH₂O—⟨⟩—CO

| Compound No. | R² | R⁴ | C-N point or C-I point (°C.) | N-I point |
|---|---|---|---|---|
| 85 | C₅H₁₁ | C₅H₁₁ | 118.8 | — |
| 86 | C₆H₁₃ | C₆H₁₃ | 120.9 | — |
| 87 | C₂H₅(CH₃)CHCH₂ | C₂H₅(CH₃)CHCH₂ | 155.2 | — |

TABLE 10

Compounds of the formula (I) wherein X =

R²OCH₂CH₂O—⟨⟩—CO and Y = R⁴

| Compound No. | R² | R⁴ | C-I point (°C.) | N-I point |
|---|---|---|---|---|
| 88 | C₂H₅ | C₄H₉ | 95.8 | — |
| 89 | C₂H₅ | C₅H₁₁ | 97 | — |
| 90 | C₃H₇ | C₄H₉ | 75.8 | — |
| 91 | C₃H₇ | C₅H₁₁ | 93.1 | — |
| 92 | C₄H₉ | C₄H₉ | 69.9 | — |
| 93 | C₄H₉ | C₅H₁₁ | 72.3 | — |

TABLE 11

Compounds of the formula (I) wherein X =

R¹—⟨⟩—CO and Y = R⁴OCH₂CH₂

| Compound No. | R¹ | R⁴ | C-I point (°C.) | N-I point (°C.) |
|---|---|---|---|---|
| 94 | C₄H₉ | C₃H₇ | 81.6 | — |

TABLE 12

| Compound No. | X | Y | C-N point or C-I point (°C.) | N-I point (°C.) |
|---|---|---|---|---|
| 95 | ⟨⟩—CO | ⟨⟩—CO | 240.3 | — |
| 96 | C₄H₉—⟨⟩—CO | C₄H₉—⟨⟩—CO | 166 | — |
| 97 | C₅H₁₁—⟨⟩—CO | C₅H₁₁—⟨⟩—CO | 147 | (137.8) |
| 98 | C₈H₁₇—⟨⟩—CO | C₈H₁₇—⟨⟩—CO | 139.8 | — |
| 99 | C₅H₁₁O—⟨⟩—CO | C₅H₁₁O—⟨⟩—CO | 158.9 | 174 |
| 100 | C₆H₁₃O—⟨⟩—CO | C₆H₁₃O—⟨⟩—CO | 150 | 170.2 |
| 101 | C₇H₁₅O—⟨⟩—CO | C₇H₁₅O—⟨⟩—CO | 154.2 | 162.4 |
| 102 | C₄H₉—⟨⟩—CO | C₆H₁₃ | 88.8 | — |
| 103 | C₅H₁₁—⟨⟩—CO | C₇H₁₅ | 84.3 | — |
| 104 | C₄H₉O—⟨⟩—CO | C₅H₁₁ | 100.7 | — |
| 105 | C₅H₁₁O—⟨⟩—CO | C₃H₇ | 94.9 | — |
| 106 | C₆H₁₃O—⟨⟩—CO | C₄H₉ | 91.6 | — |
| 107 | C₄H₉ | C₄H₉ | 190.4 | — |
| 108 | C₅H₁₁ | C₅H₁₁ | 171.8 | — |
| 109 | C₈H₁₇ | C₈H₁₇ | 147.3 | — |
| 110 | CH₃—OCH₂CH₂O | CH₃OCH₂CH₂ | 152.4 | — |

In Tables 1–12, the temperatures described in the column of C-N point or C-I point are those at which a crystal melts and transfers into a nematic phase or an isotropic phase, and correspond to C-I point in case where no temperature is described in the column of N-I point, while correspond to C-N point in case where a temperature is described therein. The temperatures described in the column of N-I point correspond to transition temperatures at which a nematic phase transfers into an isotropic phase, and those shown in the parenthese correspond to monotropic transition temperatures. The symbol (C-S) described in the column of C-N point or C-I point shows that the mesomorphic phase corresponds to a smectic phase.

Liquid crystal compounds which become a constituting component of a liquid crystal composition for display elements capable of being actuated in the temperature range in which usual liquid crystal display elements are employed, i.e. a temperature range of about −10° C. to 60° C., are, of course, preferred to have as low a melting point of crystal as possible and as high a N-I point and a S-I point as possible. Accordingly, compounds of Table 1 and those of Table 5 are generally most suitable, and can be employed in a relatively high content in liquid crystal compositions.

Compounds of Table 4 have generally a relatively high melting point, but, nevertheless, their compatibilities with other liquid crystal materials are good; hence they are easily employed as a constituting component of a liquid crystal composition. Further since they have a high N-I point, they are suitable for elevating the clearing point of liquid crystal compositions i.e. N-I point.

Compounds of Table 2 are useful because of their high N-I point. However since they are inferior to the compounds of Table 4 in the compatibility with other liquid crystal materials, attention must be paid when they are employed as a constituting component of liquid crystal compositions for general uses. In this case, a measure of the amount of single use of compounds of Table 2 may be about 3% by weight based on the total weight of a liquid crystal composition.

Compounds of Tables other than the above-mentioned are those whose liquid crystal phase could not be observed at least in their single use. However, it is presumed that these compounds, too, might have a latent nematogenic or smetogenic property in view of their similarity in the chemical structure, but, even on the assumption that they become a liquid crystal, they crystallize at a temperature higher than the transition point at which a liquid crystal is brought about; hence no liquid crystal phase could be observed. In view of such a property, it cannot be recommended to employ these compounds as a principal constituting component of liquid crystal compositions in a large proportion, but they have a possibility that they are useful for improving a certain characteristic properties of liquid crystal compositions such as viscosity, response rate, orienting property to electrode base, etc.

Most of the compounds of Tables 1–11 exhibit a nematic liquid crystal phase, and can be employed as a component of liquid crystal compositions having a large negative $\Delta\epsilon$ value, but some of them exhibit a smectic phase, and although they may be employed as a constituting component of nematic liquid crystal compositions having a large negative $\Delta\epsilon$ value, in a low concentration, they are suitable as a constituting component of smectic liquid crystal compositions having a negative dielectric anisotropy. As the uses of smectic liquid crystals having a negative dielectric anisotropy, the following ones are proposed:

A first use wherein a p type dye (a dichroic dye that the transition moment of visible ray absorption by a dye molecule is in the direction of the principal axis of the dye molecule and that is referred to also as a dichroic dye with a positive dichroism) is added to the liquid crystals, the resulting material is brought into a vertical alignment to the surface of an electrode, and a color display is brought about by impression to the electrode.

A second use wherein a smectic liquid crystal is heated to form a nematic phase through which a current is passed, to thereby form a state of a dynamic scattering, in which state it is cooled and fixed into a smectic state where light scatters to thereby form a scattering display with memory.

The values of dielectric anisotropies of representative compounds among those of the present invention are as follows:
- −17 (compound No. 16);
- −22 (compound No. 34);
- −13.5 (compound No. 58); and
- −15.1 (compound No. 22)

The simplest manner in which these values are determined is as follows:

For example, a solution obtained by dissolving 1.1 g of 2,3-dicyano-1,4-bis(trans-4-butylhexylcarboxy)benzene (compound No. 34) in 9 g of a 2:1 (by wt.) mixture of p-pentylphenyl p-methoxybenzoate with p'-pentylphenyl p-hexyloxybenzoate (this mixture having a nematic temperature range of 15°–48° C. and a $\Delta\epsilon$ value of +0.1), is sealed in a cell subjected to a vertical alignment treatment and having an electrode distance of about 10 μm, and its voltage-current characteristic is measured with a frequency of 1 KHz to give a $\Delta\epsilon$ value of −2.3, from which the $\Delta\epsilon$ value of compound No. 34 itself is calculated by extrapolation to give about −22. The $\Delta\epsilon$ values of the above shown compounds of 4 kinds are much larger than those of the above-mentioned known compounds [(II), (III) and (IV)]. This makes it easy to produce liquid crystal compositions having a large negative value of dielectric anisotropy, by employing the compounds of the present invention.

The compounds of the present invention, when subjected to measurement of ultraviolet absorption spectra in a 1% ethanol solution thereof, substantially do not absorb any ray having a wave length of 350 nm or longer. Further these compounds are chemically stable. Accordingly, even when they are mixed with any one of well known liquid crystal materials, there is no fear of damaging their chemical and photo-chemical stabilities.

The liquid crystal materials as a base to which the compounds (I) of the present invention are added, are preferred to be liquid crystals having a negative $\Delta\epsilon$ value, or even when they have a positive $\Delta\epsilon$ value, those having a small positive $\Delta\epsilon$ value. They are liquid crystal materials composed of liquid crystal substances having one of cyano group, nitro group, etc. as a substituent at p-position, that is, such as Schiff base type liquid crystal compounds exemplified by MBBA (methoxybenzylidenebutylaniline) and EBBA (ethoxybenzylidenebutylaniline), phenyl esters of benzoic acid (e.g. p'-pentylphenyl p-hexyloxybenzoate), azoxybenzene type liquid crystals (e.g. p-methoxy-p'-butylazoxybenzene, p-methoxy-p'-ethylazoxybenzene), phenyl esters of trans-alkylcyclohexanecarboxylic acid (e.g. p-ethoxyphenyl trans-4-butylcyclohexanecarboxylate), etc.

On the other hand, since the compounds (I) have a large negative dielectric anisotropy, it is also possible to add a slight amount of them to liquid crystal materials having a positive dielectric anisotropy to thereby reduce the value of the dielectric anisotropy alone, almost without changing other characteristics of liquid crystals as the base.

The compounds (I) can be synthesized according to such a method as mentioned below. Firstly, 2,3-dicyano-p-hydroquinone is employed as a common, intermediate raw material for preparing the compounds (I). The hydroquinone is a substance known from old time, and synthesized for example according to the method described in Thiele & Meisenheimer, Berichte, 33, 675 (1900). Diethers among the compounds (I) are synthesized by alkylating 2,3-dicyanohydroquinone with an alkylating agent such as p-toluenesulfonic acid esters, alkyl halides, etc. For synthesizing unsymmetrical dialkyl ethers, a sulfonic acid ester in a nearly equimolar amount to the dicyanohydroquinone may be firstly employed to obtain a monoalkylated substance, which is then converted into a dialkyl ether, with another kind of a sulfonic acid ester or an alkyl halide. The diester structure compounds among the compounds (I) may be suitably synthesized by reacting a corresponding acid halide in a basic solvent. The ester-ether structure compounds among the compounds (I) may be suitably synthesized by firstly reacting about one mol of a p-toluenesulfonic acid ester and then reacting a corresponding acid halide in a basic solvent such as pyridine. Alternatively they may be also synthesized by firstly reacting about one mol of a corresponding acid halide to obtain a monoester, which is then reacted with a 1-diazoalkane.

The present invention will be illustrated by way of Examples in more detail.

EXAMPLE 1

(Preparation of compound of No. 17)

Fifty grams of 2,3-dicyano-p-hydroquinone, 375 ml of 5% sodium hydroxide aqueous solution and 113 g of n-pentyl p-toluenesulfonate were heated in a 1 l capacity three-neck flask with stirring and under reflux for 7 hours and then transferred into a separating funnel. Toluene and an aqueous solution of sodium hydroxide were added and 2,3-dicyano-p-hydroquinone monopentyl ether and unreacted 2,3-dicyano-p-hydroquinone were extracted into an alkali aqueous layer. The resulting alkali aqueous layer was acidified with hydrochloric acid. Precipitated solid was collected and dissolved in 1 l of toluene, followed by filtration while hot, whereby unreacted 2,3-dicyano-hydroquinone was almost thoroughly removed. On cooling the filtrate (toluene solution), raw 2,3-dicyano-p-hydroquinone monopentyl ether precipitated, followed by filtering off and recrystallization from an aqueous methanol to obtain a crystal having a m.p. of 150°–153° C. (yield: 21 g). On the other hand, 19.8 g of trans-p-pentylcyclohexanecarboxylic acid and 5.0 ml of thionyl chloride were heated under reflux for 40 minutes, and excessive thionyl chloride was distilled off to obtain an acid chloride, which was then turned to 100 ml of a toluene solution, which was then dropwise added, on water-cooling and with stirring, to a solution obtained by dissolving 20 g of 2,3-dicyano-p-hydroquinone monopentyl ether obtained above, in pyridine. The resulting material was heated with stirring at 50° C. for one hour and then cooled, followed by adding ice and 6 N hydrochloric acid to acidify it, adding 200 ml of toluene, separation, water-washing, washing with 2 N aqueous sodium hydroxide, again water-washing, distilling off of toluene and recrystallization of the resulting residue from ethanol to obtain 31.7 g of a colorless crystal of objective 3-pentyloxy-6-(trans-4'-n-pentylcyclohexanecarboxy)-phthalonitrile. This crystal once melted at 95° C. to form an acicular crystal in the melt. This acicular crystal melted at 101.5° C. to form an isotropic liquid, which, on cooling, turned to a nematic liquid crystal (monotropic at 76°–77° C.

Other 2,3-dicyano-p-hydroquinone monoalkyl ethers as intermediates showed the following melting points:

2,3-dicyano-p-hydroquinone monopropyl ether: 175°~176° C.

2,3-dicyano-p-hydroquinone monobutyl ether: 157°~159° C.

2,3-dicyano-p-hydroquinone monohexyl ether: 147°~149° C.

2,3-dicyano-p-hydroquinone monoheptyl ether: 146°~149° C.

2,3-dicyano-p-hydroquinone monooctyl ether: 143°~147° C.

2,3-dicyano-p-hydroquinone β-propoxyethyl ether: 115°~118° C.

2,3-dicyano-p-hydroquinone β-ethoxyethyl ether: 167°~170° C.

2,3-dicyano-p-hydroquinone β-methoxyethyl ether: 192.3°~194° C.

Figure 1:
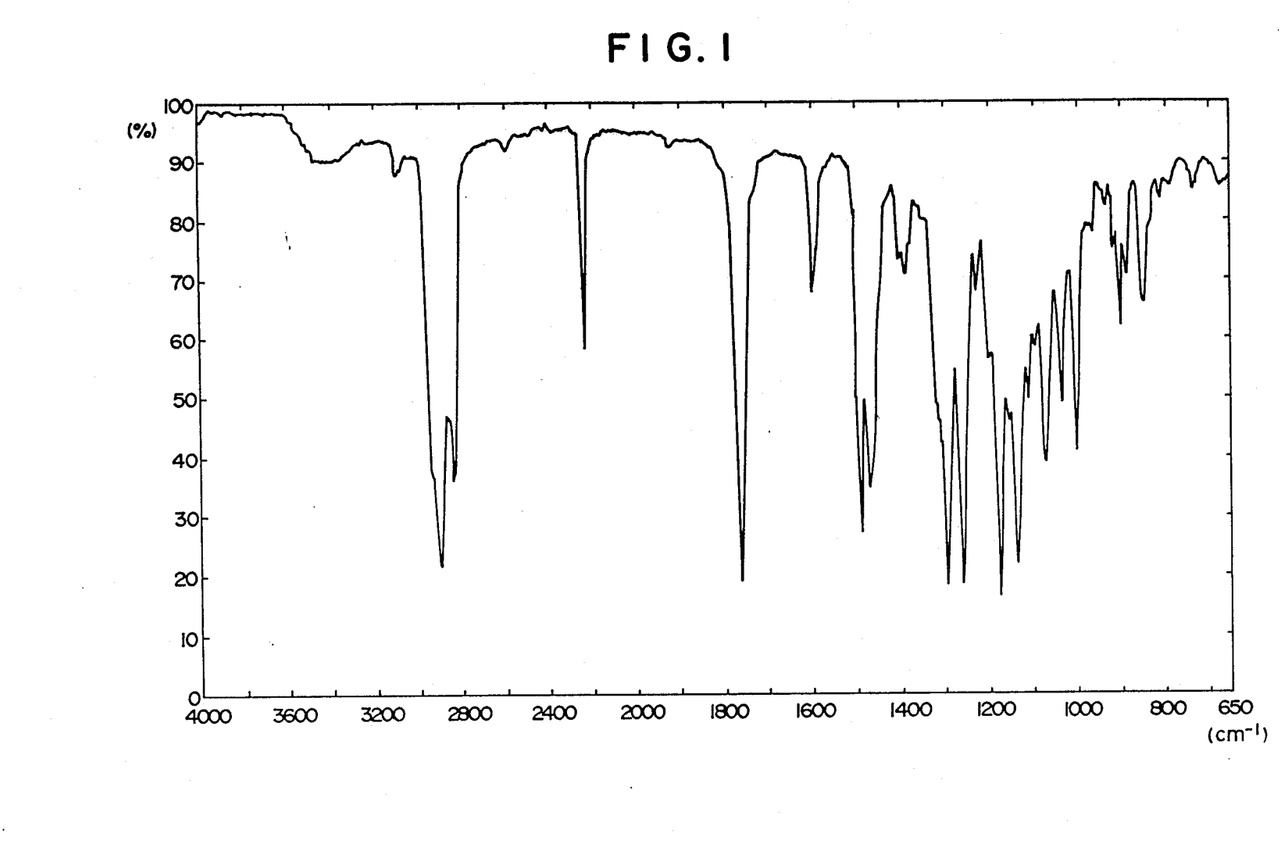
Figure 2:
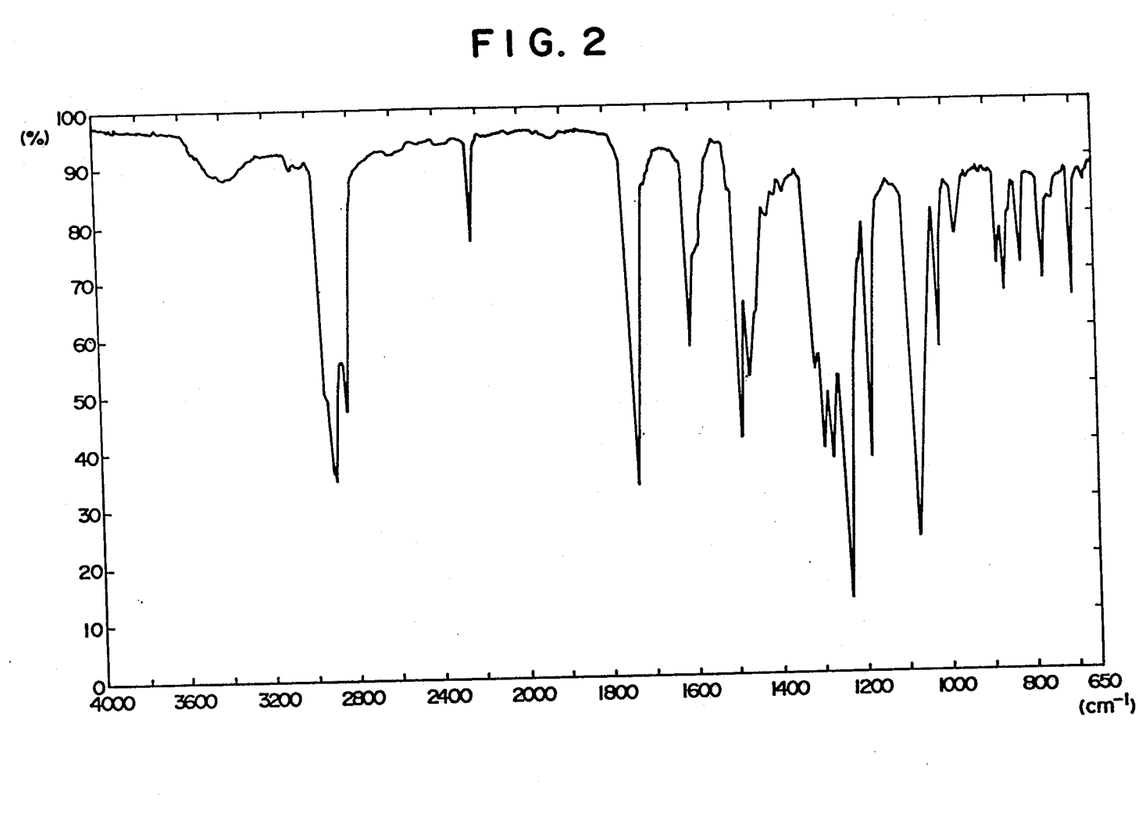

Compounds Nos. 1–31, 39–82, 88–94 and 102–106 were synthesized in a similar manner to that of this Example. Infrared ray absorption spectra of compounds No. 4 and No. 56 among the above-mentioned compounds are shown in FIG. 1 and FIG. 2.

EXAMPLE 2

(Preparation of compound No. 16)

18.4 Grams of trans-p-butylcyclohexanecarboxylic acid and 50 ml of thionyl chloride were heated under reflux for 40 minutes, followed by distilling off excessive thionyl chloride to obtain an acid chloride. On the other hand, 16 g of 2,3-dicyano-p-hydroquinone was dissolved in 60 ml of pyridine, and to the resulting solution was dropwise added a toluene solution of the acid chloride obtained above on water-cooling with stirring, followed by further heating at 50° C. and stirring for 30 minutes. To the resulting material were added ice and 6 N hydrochloric acid, and the resulting precipitate was filtered and collected, followed by recrystallizing it from an aqueous methanol and then from toluene to obtain 10.3 g of a crystal having a m.p. of 153°–154° C., which was trans-p-n-butylcyclohexanecarboxylic acid monoester of 2,3-dicyano-p-hydroquinone. Five grams of this monoester were dissolved in 100 ml of ether, and cooled to 0° C. An ether solution of a slight excess amount of diazopentane was dropwise added to the cooled solution, followed by allowing the resulting material to stand at room temperature for 5 hours, distilling off of ether under reduced pressure and recrystallization of the resulting residue from ethanol to obtain 5.1 g of a colorless crystal of objective 3-n-pentyloxy-6-(trans-4'-n-butylcylohexanecarboxy)-phthalonitrile, which gave an isotropic liquid at a m.p. of 82°–83° C. and gave a nematic liquid crystal (monotropic) at 66°–67° C.

Diazopentane employed here was synthesized according to the method described in D. W. Adamson and J. Kenner, J. Chem. Soc., 1935, p. 286 and J. Chem. Soc., 1937, p. 1551.

EXAMPLE 3

(Preparation of compound No. 36)

46 Grams (0.22 mol) of trans-4-n-hexylcyclohexanecarboxylic acid together with 50 ml of thionyl chloride and 100 ml of toluene were heated in a flask equipped with a reflux condenser on a water bath for 40 minutes, and excessive thionyl chloride and about 30 ml of toluene were distilled off. On the other hand, 16 g (0.1 mol) of 2,3-dicyano-1,4-hydroquinone were dissolved in a solvent mixture of 300 ml of pyridine with 600 ml of toluene and cooled with water, followed by stirring. To this solution was dropwise added a toluene solution of the acid chloride of the carboxylic acid obtained above, over 20 minutes, followed by continuing stirring for 10 minutes and then heating with stirring on a water bath for 40 minutes. After ice-cooling, 6 N hydrochloric acid was dropwise added to acidify the solution, followed by separation, washing the resulting organic layer with 6 N hydrochloric acid, then a saturated sodium chloride aqueous solution, and further with 2 N sodium hydroxide, a saturated sodium chloride aqueous solution, and water in this order, and then distilling off toluene, to obtain a crystal as a residue. This crystal was recrystallized from ethanol to obtain 30.6 g of a colorless crystal of objective 2,3-dicyano-1,4-bis(trans-4-hexylcyclohexylcarboxy)benzene (yield: 68.4% based on 2,4-dicyano-1,4-hydroquinone). This crystal gave a nematic liquid crystal at a m.p. of 131.5° C. and gave an isotropic liquid at 206° C. Further, the fact that this crystal was the objective compound was confirmed by the following elemental analysis values and infrared absorption spectra shown in FIG. 3.

Figure 3:
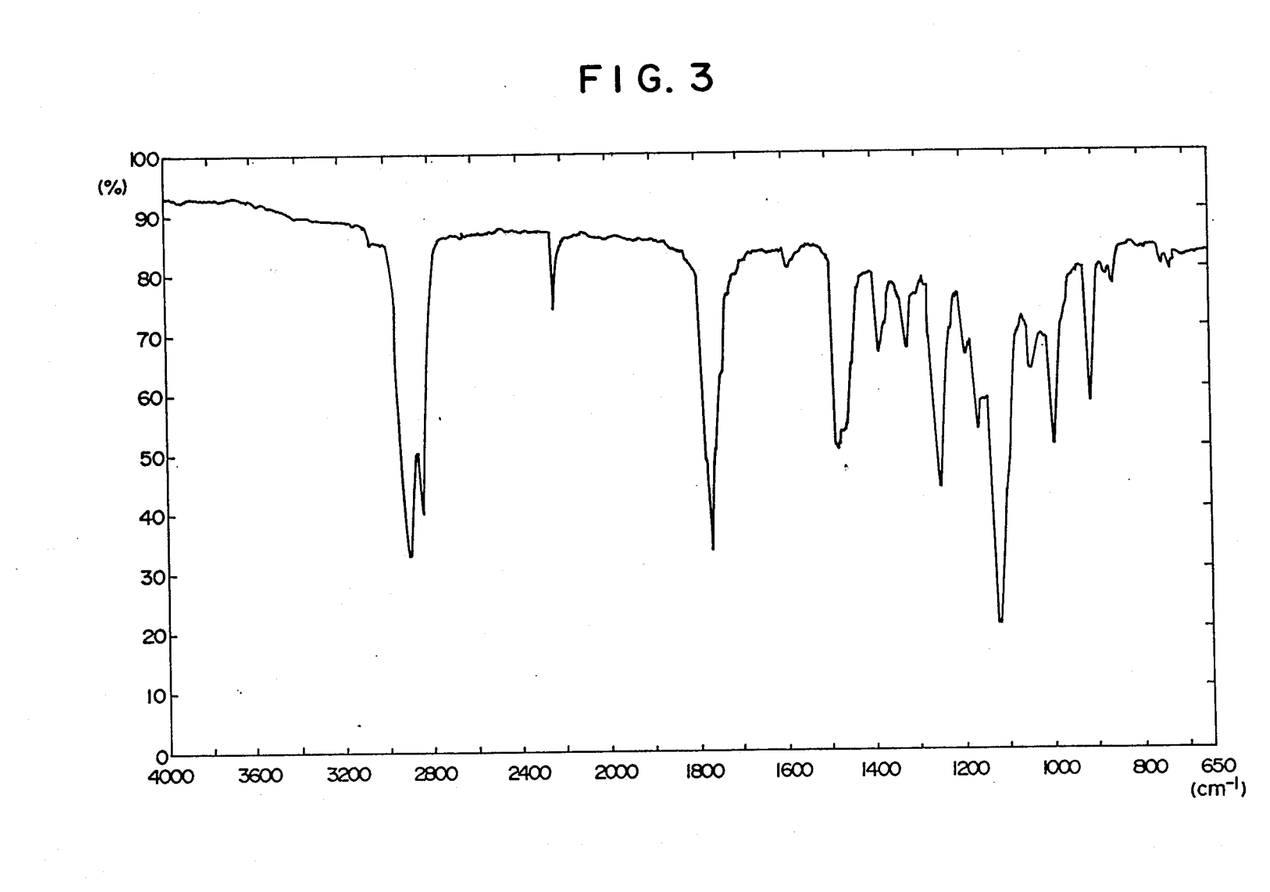

| Name of element | Analytical value | Calculated value (in terms of $C_{34}H_{48}N_2O_4$) |
| --- | --- | --- |
| C | 74.6% | 74.41% |
| H | 8.8% | 8.82% |
| N | 5.0% | 5.1% |

Compounds Nos. 32–38, 83–87 and 95–101 were also synthesized in a similar manner to that of this Example.

EXAMPLE 4

(Use example 1)

A liquid crystal mixture consisting of 2 parts of p'-pentylphenyl p-methoxybenzoate and one part of p'-pentylphenyl p-hexyloxybenzoate has a nematic temperature range of 15°–48° C. and a $\Delta\epsilon$ of +0.1, and was employed as a base liquid crystal in this Example. Compounds of the formula (I) were mixed with 9 g of the base, as shown in Table 13. Further, 1% by weight of a dye (D-16 or D-27 made by BDH company) was added as a guest. The resulting material was sealed in a liquid crystal cell having a cell gap of about 10 μm and subjected to a vertical alignment treatment, followed by impressing a voltage of 1 KHz to observe a so-called guest-host effect. Thus the results shown in Table 13 were obtained. Measurement was carried out at a light transmittance of 600 nm in the case of the dye D-16 and at a light transmittance of 610 nm in the case of the dye D-27.

TABLE 13

| Added compound (I) | Added amount (g) | $\Delta\epsilon$ | Dye | $V_{th}$ (volt) | $V_{sat}$ (volt) |
| --- | --- | --- | --- | --- | --- |
| No. 18 | 0.9 | −1.5 | D-16 | 3.0 | 4.0 |
| No. 11 | 0.9 | −1.5 | D-16 | 3.0 | 4.0 |
| Mixture of Nos. 2, 3, 4, 5 and 6 in a ratio by weight of 1:1:1:1:1 | 1.0 | −.15 | D-27 | 3.6 | 5.0 |
| No. 34 | 1.1 | −2.3 | D-16 | 3.3 | 4.5 |
| Mixture of Nos. 46, 51, 56, 62 and 64 in a ratio by weight of 2:1:3:2:2 | 1.13 | −2.3 | D-27 | 1.6 | 2.4 |

$V_{th}$: Threshold voltage
$V_{sat}$: Saturated voltage

EXAMPLE 5

(Use example 2)

A liquid crystal composition consisting of 33.5 parts of p'-n-pentylphenyl p-methoxybenzoate, 16.5 parts of p'-n-pentylphenyl p-hexyloxybenzoate, 16.5 parts of p'-ethoxyphenyl trans-4-n-butylcyclohexanecarboxylate, and 33.5 parts of p'-hexyloxyphenyl trans-4-n-butylcyclohexanecarboxylate, has a negative $\Delta\epsilon$ and a N-I point of 58.4° C., and even when it is preserved at −5° C. for a long time, no precipitation of crystal is observed. To this mixture was added 1% by weight of an anthraquinone dye (D-16 made by BDH Company) as a guest, and the resulting material was sealed in a cell having a thickness of 10 μm and subjected to a vertical alignment treatment, followed by measuring the variation of light transmittance by voltage with a light having a wave length of 600 nm to thereby observe its guest-host effect and seek its actuation characteristics. As a result, its threshold voltage was 4.8 V and its saturated voltage was 6.3 V.

On the other hand, compounds of the formula (I) were mixed with 80 parts of the above-mentioned base liquid crystal, as shown in Table 14, and to the resulting mixtures was further added 1% by weight of a dye D-16 (made by BDH Company) as a guest, followed by similarly observing their guest-host effects. The results are shown in Table 14.

TABLE 14

| Added compounds | Added amount | $\Delta\epsilon$ | N-I point (°C.) | $V_{th}$ (volt) | $V_{sat}$ (volt) |
| --- | --- | --- | --- | --- | --- |
| Mixture of compounds Nos. 17, 18 and 19 in a ratio by weight of 3:4:3 | 20 parts | −3.8 | 50.5 | 1.7 | 2.6 |
| Mixture of compounds Nos. 33, 34 and 35 in a ratio by weight of 3:3:4 | 8.89 parts | −2.3 | 66.4 | 3.2 | 4.5 |
| Mixture of compounds Nos. 4, 5 and 19 in a ratio by weight of 3:4:3 | 20 parts | −3.2 | 44.0 | 1.9 | 2.9 |
| Mixture of compounds Nos. 9, 10 and 11 in a ratio by weight of 3:3:4 | 20 parts | −3.8 | 46.9 | 1.7 | 2.6 |

EXAMPLE 6

(Use example 3)

One percent by weight of an anthraquinone dye D-52 (made by BDH Company) was added to the same base liquid crystal as that employed in Example 5, and the guest-host effect was measured in the same manner as in Example 5, but a light having a wave length of 540 nm was employed in the measurement. Its threshold voltage was 4.8 V and its saturated voltage was 6.3 V. On the other hand, compounds of the formula (I) were added to 75 parts of the base liquid crystal, as shown in Table 15, and to the resulting mixture was added 1% by weight of a dye D-52, followed by the same measurement as in Example 5. The results are shown in Table 15.

TABLE 15

| Added compounds | Added amount | $\Delta\epsilon$ | N-I point (°C.) | $V_{th}$ (volt) | $V_{sat}$ (volt) |
|---|---|---|---|---|---|
| Mixture of compounds Nos. 7, 14 and 22 in a ratio by weight of 1:1:1 | 13.4 parts | −3.8 | 50.3 | 1.8 | 2.8 |
| Mixture of compounds Nos. 9, 16, 18, 22 and 41 in a ratio by weight of 1:1:1:1 = 1 | 25 parts | −4.3 | 47.0 | 1.5 | 2.4 |
| Mixture of compounds Nos. 10, 16, 65, 66, 67 and 94 in a ratio by weight of 4:5:4:4:4:4 | 25 parts | −4.4 | 59.2 | 1.5 | 2.5 |

EXAMPLE 7

(Use example 4)

A liquid crystal mixture was prepared which consisted of compounds Nos. 9, 15, 16 and 17 (each 5.1 parts);
p'-butoxyphenyl trans-4-n-propylcyclohexanecarboxylate,
p'-butoxyphenyl trans-4-n-butylcyclohexanecarboxylate,
p'-hexyloxyphenyl trans-4-n-butylcyclohexanecarboxylate and
p'-methoxyphenyl trans-4-n-pentylcyclohexanecarboxylate (each 13.3 part);
4-n-pentyl-n-hexyloxybiphenyl (10.2 parts); and
4-n-pentyl-4'-ethoxybiphenyl (16.2 parts).

This liquid crystal composition had a N-I point of 57° C., a viscosity of 65 cp at 25° C. and a dielectric anisotropy of −5.1.

EXAMPLE 8

(Use example 5)

A liquid crystal mixture was prepared which consisted of
compounds Nos. 9, 10 and 11 (each 4 parts);
compounds Nos. 55 and 56 (each 5 parts);
p'-butoxyphenyl trans-4-n-propylcyclohexanecarboxylate,
p'-ethoxyphenyl trans-4-n-butylcyclohexanecarboxylate,
p'-methoxyphenyl trans-4-n-butylcyclohexanecarboxylate,
p'-ethoxyphenyl trans-4-n-propylcyclohexanecarboxylate and
p'-methoxyphenyl trans-4-n-pentylcyclohexanecarboxylate (each 10 parts); and
p'-n-propylphenyl p-n-hexanoyloxybenzoate,
p'-n-heptylphenyl p-n-hexanoyloxybenzoate, and
p'-n-hexyloxyphenyl p-n-butylbenzoate (each 6 parts); and
a liquid crystal mixture, ZLI 1275 made by Merck Company (10 parts).

No crystal precipitated from this liquid crystal mixture even when the mixture was preserved at −15° C. for a long time. This mixture had a N-I point of 68° C., a dielectric anisotropy of −5.1 and a viscosity of 60 cp at 25° C. Its guest-host effect was measured employing a dye D-16 made by BDH Company to give a $V_{th}$ of 1.5 volt, a $V_{sat}$ of 2.5 volt, and response times of 95 msec ($\tau_{rise}$) and 280 msec ($\tau_{decay}$). (The measurement was carried out at 25° C., at a cell gap of 10 μm and at an impressed voltage of 3 V).

What is claimed is:

1. Compounds expressed by the general formula (I)

wherein X represents

Y represents $R^4$, $R^1$ and $R^3$ each represent an alkyl group or an alkyloxy group of 1–10 carbon atoms; and
$R^4$ represents an alkyl group of 1–10 carbon atoms.

2. Compounds according to claim 1 wherein and $Y = R^4$.

3. Compounds according to claim 1 wherein

$X = R^1$—⟨ ⟩∥∥ CO and $Y = R^3$—⟨ ⟩∥∥ CO.

4. Compounds according to claim 1 wherein and Y=R⁴—O—CH₂CH₂.

5. Compounds according to claim 1 wherein and Y=R⁴.

6. Compounds according to claim 1 wherein and Y=R⁴—O—CH₂CH₂.

7. Liquid crystal compositions comprising at least one compound of the general formula (I) of claim 1, and having a negative dielectric anisotropy.

8. Liquid crystal compositions comprising at least one compound of formula (I) of claim 1, and having a negative dielectric anisotropy of −3 or less.

9. Liquid crystal display elements obtained by adding 0.5 to 3.0% by weight of a dye having a positive dichroism to the liquid crystal compositions of claim 7 or claim 8 to thereby utilize the guest-host effect of the resulting mixture.

10. Liquid crystal display elements obtained by adding dye having a positive dichroism and a dye having a negative dichroism to the liquid crystal compositions of claim 7 or claim 8 to thereby utilize the guest-host effect of the resulting mixture.

* * * * *